United States Patent [19]

Aga et al.

[11] Patent Number: 5,556,866
[45] Date of Patent: Sep. 17, 1996

[54] HAIR RESTORER AND ITS PREPARATION

[75] Inventors: Hajime Aga; Takashi Shibuya; Toshiyuki Sugimoto; Toshio Miyake, all of Okayama, Japan

[73] Assignee: Kabushiki Kaisha Hayashibara Seibutsu Kagaku Kenkyujo, Okayama, Japan

[21] Appl. No.: 234,384

[22] Filed: Apr. 28, 1994

[30] Foreign Application Priority Data

Apr. 28, 1993 [JP] Japan .................................. 5-123223

[51] Int. Cl.$^6$ .................... A61K 31/44; A61K 31/42; A61K 31/19; A61K 31/235
[52] U.S. Cl. .................... 514/332; 514/374; 514/533; 514/570
[58] Field of Search .................................. 514/533, 570, 514/332, 374

[56] References Cited

FOREIGN PATENT DOCUMENTS 461827 12/1991 European Pat. Off. .
0529962 3/1992 European Pat. Off. .
16384185 8/1985 Japan .

OTHER PUBLICATIONS

Fujimura; *3-(4-Hydroxyphenyl)-2-(E)-PR Openic Acid;* Patent Abstracts of Japan; vol. 10, No. 4; C-322; 09 Jan. 1986.
*3-[4-Hydroxy-3-[3-(hydroxymethyl)-2-butenyl]-5-(3-methyl-2-butenyl) Phenyl]-2(E)-propenoic acid;* Chemical Abstracts; vol. 101, No. 25; 17 Dec. 1984.
Zdero, C. et al. "Diterpene Glycosides and Other Constituents from Argentinian Baccharis Species." 1986.
Okuno, Isamu, et al. "Studies on Choleretic Constituents in *Artemisia capillaris* Thun B." Chem. Pharm. Bull. 36(2) 769–775 (1988).

*Primary Examiner*—Phyllis G. Spivack
*Attorney, Agent, or Firm*—Browdy and Neimark

[57] ABSTRACT

A hair restorer which comprises a carrier and an effective amount of one or more compounds selected from the group consisting of 3-[4-hydroxy-3,5-bis(3-methyl-2-butenyl)phenyl]-2-propenoic acid, benzenepropanoic acid 4-(2-carboxyethenyl)-2-(3-methyl-2-butenyl)phenylester, and their salts, in the treatment and prevention of alopecia.

12 Claims, 4 Drawing Sheets

HAIR RESTORER AND ITS PREPARATION

FIELD OF THE INVENTION

The present invention relates to a novel hair restorer, more particularly, to a hair restorer which comprises a carrier and an effective amount of one or more compounds selected from the group consisting of 3-[4-hydroxy-3,5-bis(3-methyl-2-butenyl)phenyl]-2-propenoic acid, benzenepropanoic acid 4-(2-carboxyethenyl)-2-(3-methyl-2-butenyl)phenylester, and their salts, as well as to the preparation of said hair restorer.

BACKGROUND OF THE INVENTION

Maintaining healthy hair is a common wish. The present inventors had studied propolis extract and its functions. As a result, we had established a purified propolis extract, which exerts an activity on the growth of hair, as well as its preparation and uses, and disclosed them in Japanese Patent Application No. 269,038/92. The reality of the substance exerting such an activity, however, had not yet been revealed. There has been a great demand to reveal the substance and establish a hair restorer which exerts a strong activity on the growth of hair without a fear of causing side effects.

SUMMARY OF THE INVENTION

The object of the present invention is to provide a hair restorer which comprises a carrier and a compound(s) as an effective ingredient capable of exerting a strong activity on the growth and regeneration of hair without fear of causing side effects.

In order to attain the aforesaid object, the present inventors have eagerly conducted studies on propolis extract. As a result, we found that 3-[ 4-hydroxy-3,5-bis(3-methyl-2-butenyl)phenyl]-2-propenoic acid (designated as "compound (1)" hereinafter) and benzenepropanoic acid 4-(2-carboxyethenyl)-2 -(3-methyl-2-butenyl)phenylester (designated as "compound (2)" hereinafter) exert a strong activity on the growth and regeneration of hair. Based on this finding, the present inventors further studied and established a hair restorer which comprises a carrier and an effective amount of one or more compounds selected from the group consisting of 3-[4-hydroxy- 3,5-bis(3-methyl-2-butenyl)phenyl] -2-propenoic acid, benzenepropanoic acid 4-(2-carboxyethenyl)-2-(3-methyl-2-butenyl)phenylester, and their salts, more particularly, we established cosmetic- and pharmaceutical-compositions which exert a strong activity on the growth and regeneration of hair, and accomplished this invention.

Thus, the present invention relates to a hair restorer which comprises a carrier and an effective amount of one or more members selected from the compounds (1) and (2) as well as their salts, and to the preparation of said hair restorer.

DETAILED DESCRIPTION OF THE INVENTION

Figure 1:
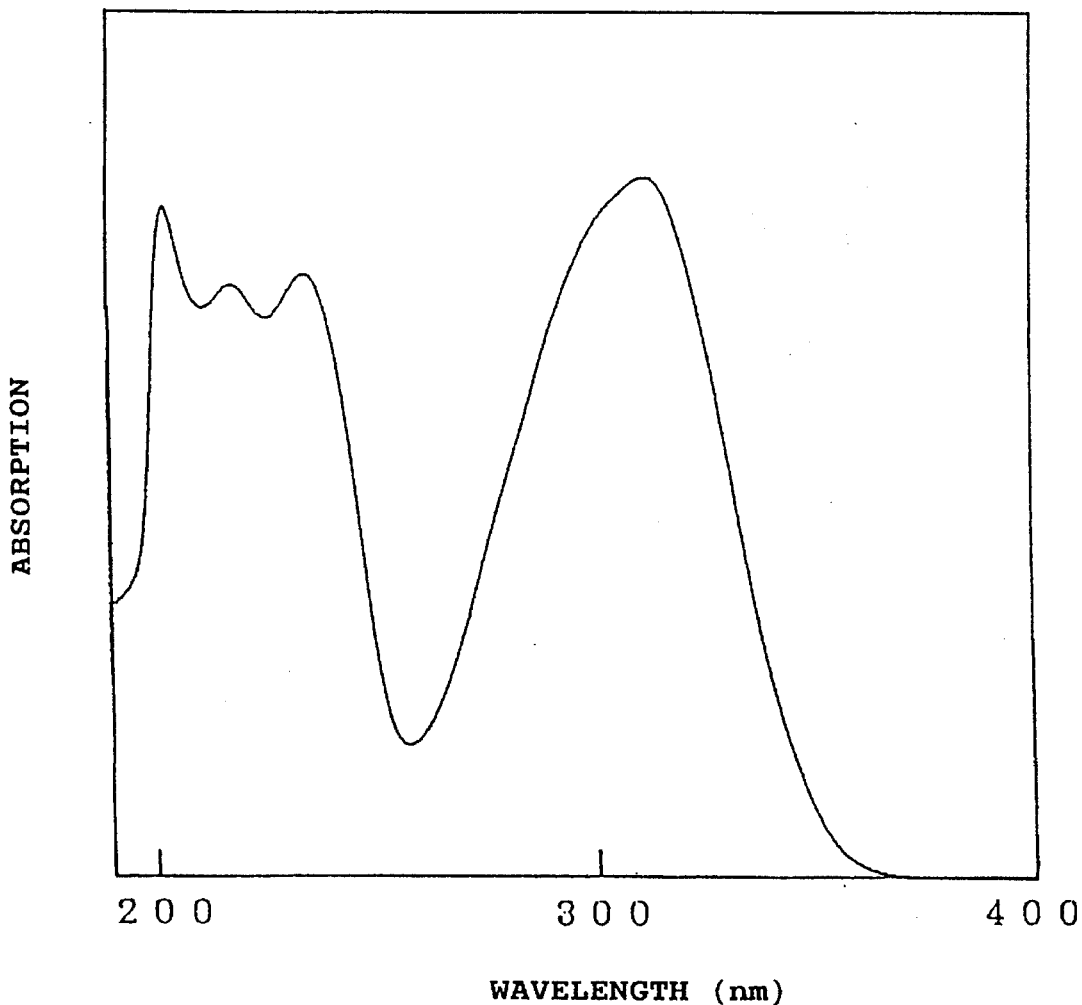
FIG. 1 shows an ultraviolet absorption spectrum of the compound (1).

The salts of the compounds (1) and (2) usable in the present invention in a variety of hair restorers, for example, those which are used in cosmetic- and pharmaceutical-compositions, i.e., those in the form of sodium-, calcium-, copper-, zinc- and silver-salts.

The hair restorer according to the present invention is in a cosmetic- or a pharmaceutical-composition from which is directed to use for the promotion of growth and regeneration of hair such as capillus and supercilium.

The compounds (1) and (2) as well as their salts are usable in accordance with the invention and are known compounds which are preparable in synthetic manner by conventional methods and preparable by extraction from plants, etc., containing these compounds and salts. The methods used to prepare these compounds and salts from natural sources in the invention include, for example, those which are preparable from propolis as well as leaves and stems of plants of the genus Compositae, e.g. *Artemisia capillaris* Thunb., as reported in *Phytochemistry*, Vol. 25, pp. 2,841–2,855 (1986) and *Chemical Pharmaceutical Bulletin*, Vol. 36, pp. 769–775 (1988). In the case of preparing these compounds (1) and (2) as well as their salts from those natural sources, they need not necessarily be isolated in a crystalline form, and can be in the form of an extract purified partially up to an extent where they exert an activity on the growth and regeneration of hair as an effective ingredient.

Conventional extractions and purifications can be appropriately used as the aforementioned preparations. For example, the compounds (1) and (2) as well as their salts can be prepared by pulverizing propolis as well as leaves and stems of plants of the genus Compositae, extracting from the resultant powder with alcohols such as methanol and ethanol, as well as their aqueous solutions, concentrating the resultant extract in usual manner, and feeding the concentrate, for example, to gel filtration column chromatography or reverse-phase column chromatography.

The compound (1) can be prepared by a chemical synthesis as disclosed in Japanese Patent Laid-Open No. 163,841/85.

The present hair restorer contains as an effective ingredient one or more members selected from the group consisting of the compounds (1) and (2) as well as their salts.

These compounds and salts usable in the invention include those which are obtainable by synthetic methods as well as those in the form of pure and crude preparations such as extracts derived from natural sources.

The carriers usable in the present hair restorer are incorporated thereinto to give a satisfactory shape and property: For example, pharmaceutically-acceptable solvents such as water-soluble solvents and organic solvents, and excipients or bases such as those for ointments can be suitably used.

Although the quantity or concentration of one or more compounds selected from the compounds (1) and (2) as well as their salts incorporated into the present hair restorer can be varied depend on the precise active agent selected, the alopecia to be treated, and symptoms and individual differences of patients, such quantity or concentration is usually in the range of about 0.01–10 w/w % (the wording "w/w %" is abbreviated as "%" hereinafter, unless otherwise specified), preferably, about 0.5–10%, more preferably 0.5–5.0%.

The present hair restorer can be formulated in usual forms such as a liquid, jelly, milk, aerosol and ointment, for example, a hair tonic, hair liquid, hair lotion, hair cream, hair oil, hair treatment, mousse, shampoo. and rinse.

Into the present hair restorer can be appropriately incorporated other substances which are used in conventional hair restorers, for example, an emollient, emulsifier, gel-imparting agent, flavor, antiseptic, antioxidant, coloring agent, refrigerant, bactericide, humectant and extract such as rosemary extract. If necessary, the effective ingredients of the present invention can be used in combination with medicaments, for example, vitamins such as vitamin E which exerts an activity on the growth and regeneration of human and animal hair, hormones, amino acids, vasohypotonics, hemokinesis-promoting agents, cell activators, anti-inflammatories, keratolytic and hyperergic agents for skin.

Especially, humectants such as propylene glycol, 1,3-butylene glycol, glycerine, sorbitol, 2-octyldodecyl myristate, polyoxyethylene polyoxypropylene glycol, and lauric acid diethanolamide facilitate the contact of the present effective ingredients with human and animal skin, accelerate the adsorption of the present effective ingredients to the skin, and attain a satisfactory growth and regeneration of hair without stimulating the skin.

"KANKOSO 301", 6-[2-[(5-bromo-2-pyridyl)amino]vinyl] -1-ethyl-2-picolinium iodide and "KANKOSO 401", 2-(2 -anilinovinyl)-3,4-dimethyloxazolium iodide, both of which are commercialized by Nippon Kankoh-Shikiso Kenkyusho Co., Ltd., Okayama, Japan, can be suitably used in the present invention as a cyanine dye. The combination use of the cyanine dyes and the effective ingredients of the present invention exerts a synergistic effect on human and animals, and attains a satisfactorily-high efficacy on the growth and regeneration of hair. The concentration of the cyanine dyes to be incorporated into the present hair restorer are usually in the range of about 0.001–0.01%.

The present hair restorer has a relatively-high commercial value because it has a relatively-long shelf life and exerts a relatively-high efficacy on the growth and regeneration of hair when applied to human and animal skin. Therefore, the present hair restorer accelerates the growth and regeneration of hair, improves the symptom of alopecia such as senile alopecia, alopecia prematura, alopecia presenilis, alopecia areata, mechanical alopecia and symptomatic alopecia, and exerts a strong efficacy on the prevention and treatment of dandruff, itch, canities and falling hair. The hair restorer according to the present invention promotes the growth and regeneration of hair or fur of animals, whose hair or fur is commercially valuable, such as sheep, fox, alpaca, Angora rabbit, mink and Cashmere goat, as well as improving their color, gloss and commercial values. The present hair restorer also improves the quality of hair, fur and feather of pet animals and birds such as dog, cat, parakeet and canary.

The present hair restorer is usually applied to a hair-growing site one to three times a day. The effective ingredients of the present invention, which are dissociative in an aqueous solution, can be iontophoresed by using a low-frequency therapeutic apparatus as disclosed in Japanese Patent Publication No. 41,747/84 and Japanese Patent Laid-Open No. 56,060/89 to attain a more satisfactory effect on the growth and regeneration of hair.

Among conventional hair restorers, those which contain substances as an active ingredient only dissolvable in either oily bases or aqueous bases and exerting a satisfactorily-high efficacy on the growth and regeneration of hair, are considerably-highly restricted in their form. This is one of disadvantages of conventional hair restorers. The effective ingredients of the present invention are readily mixed with both aqueous- and oily-bases in an effective amount, and because of this the present hair restorer has the advantage of being more easily formulated and used.

The present invention is explained in detail by the following Examples of Preparation and Examples of Experiment of the compounds (1) and (2):

Example of Preparation 1

Preparation of Compound (1)

153.3 parts by weight of a mass of crude propolis from Brazil was pulverized with "TRIO BLENDER", a product of Trio Science Co., Ltd., Tokyo, Japan, and extracted with ethyl acetate. The resultant extract was added with methanol, and the formed precipitate was removed by centrifugation. The resultant supernatant was subjected to a rotary evaporator to remove the remaining solvent, and mixed with methanol to form a precipitate which was then removed by centrifugation. The remaining supernatant was subjected to a rotary evaporator to remove the remaining solvent, and further mixed with methanol to obtain an extract in a yield of 63.9 parts by weight, on a dry solid basis (d.s.b.).

The extract was subjected to column chromatography using "SILICA GEL 60 G650", a product of Katayama Chemical Industries Co., Ltd., Tokyo, Japan, in a manner that 35 parts by weight of the extract, d.s.b., was fed to the column and eluted therefrom by gradient elution using a mixture solvent of hexane and ethyl acetate. Fractions eluted with a solvent system of hexane:ethyl acetate (=59:41–57:43 by volume) were recovered in a total yield of 2.2 parts by weight, d.s.b.

The fractions thus obtained were pooled and fed to column chromatography using "SEPHADEX LH-20", a carrier of Pharmacia LKB Biotechnology AB, Uppsala, Sweden. By using methanol as an eluent, the objective product was eluted at a flow rate of SV (space velocity) 0.16. Fractions eluted at an elution position of around 1.1 (=volume of eluate/volume of carrier) were pooled and concentrated to form a crystal which was then washed with hexane to obtain a crystalline compound in a yield of 0.28 parts by weight, d.s.b.

The physicochemical properties of the crystalline compound were studied:

(1) Melting point; 95° C.

(2) Elemental analysis;

Measured: C=75.85% H=8.39% O=16.39%

Calculated: C=75.97% H=8.05% O=15.98%

(for molecular formula $C_{19}H_{24}O_3$)

(3) Molecular weight; 300.40

(4) Ultraviolet absorption spectrum;

The crystalline compound was dissolved in methanol and determined its ultraviolet absorption spectrum. The result was as shown in FIG. 1. As evident from FIG. 1, it showed the maximum absorption peaks at wavelengths of 204 nm, 219 nm, 235 nm and 313 nm. These data correspond to those of a compound described in Japanese Patent Laid-Open No.163,841/85.

(5) Infrared absorption spectrum;

One and half mg of the crystalline compound and 200 mg of dried KBr were mixed and formed into a tablet, followed by the measurement of its infrared absorption spectrum.

Figure 2:
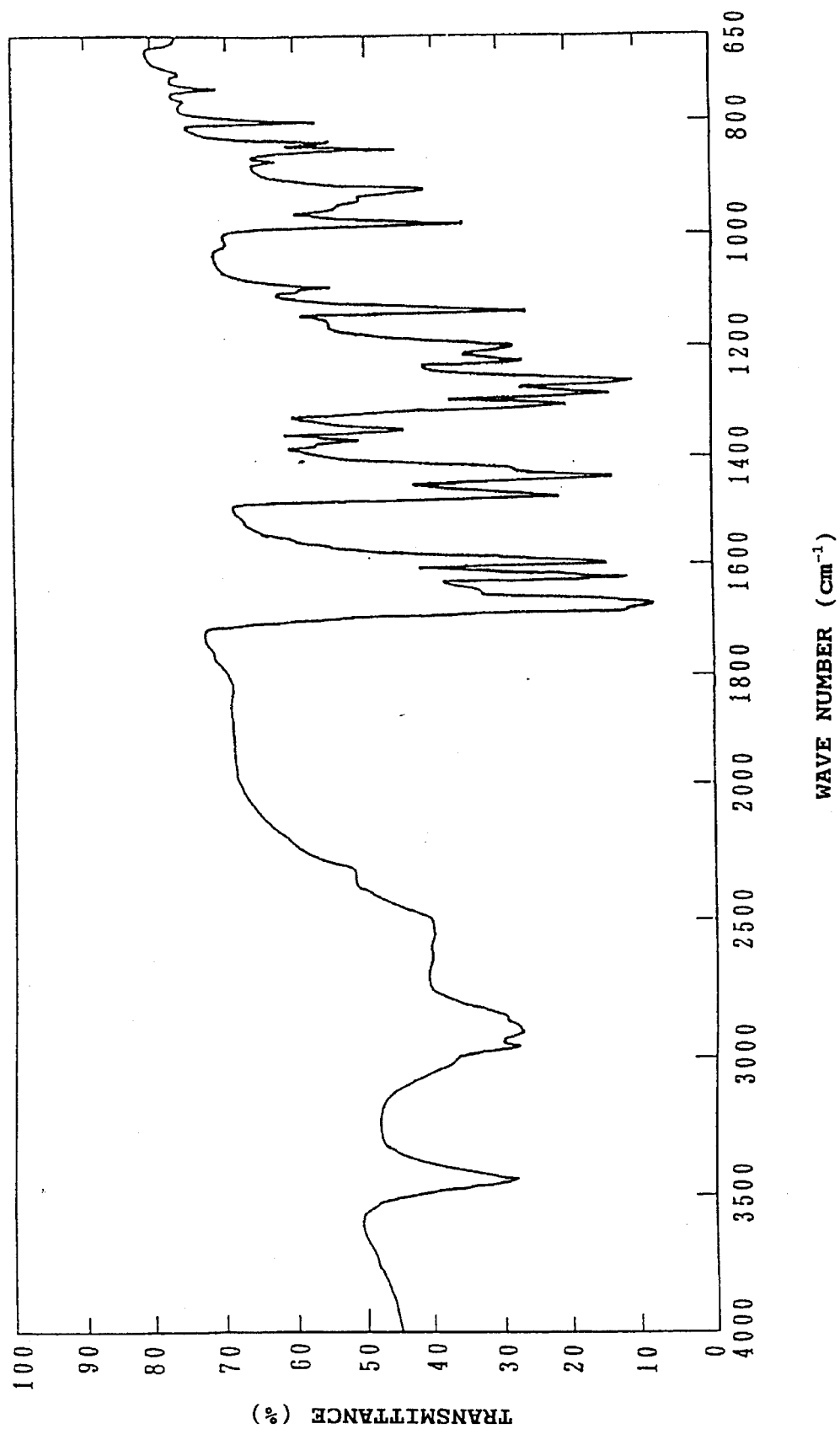
FIG. 2 shows an infrared absorption spectrum of the compound (1).

The result was as shown in FIG. 2.

As evident from FIG. 2, it has absorption peaks at wave numbers of 3440 $cm^{-1}$, 3000–2500 $cm^{-1}$ (br), 1670 $cm^{-1}$, 1625 $cm^{-1}$ and 1595 $cm^{-1}$. These absorption peaks correspond to those of the compound, described in Japanese Patent Laid-Open No. 163,841/85, having absorption peaks at wave numbers of 3440 $cm^{-1}$, 2800–2500 $cm^{-1}$ (br), 1680 $cm^{-1}$, 1628 $cm^{-1}$, 1599 $cm^{-1}$, etc.

(6) Analysis on nuclear magnetic resonance ($^1$H-NMR);

The crystalline compound was dissolved in deuterochloroform and measured its NMR with 500 MHz. The following 22 signals for hydrogen atom were found: 7.69 ppm (1 H, d, J=15.9 Hz), 7.20 ppm (2 H, s), 6.29 ppm (1 H, d, J=15.9 Hz), 5.31 ppm (2 H, br t), 3.35 ppm (4 H, br d), 1.79 ppm (6 H, s) and 1.78 ppm (6 H, s).

These signals correspond to those of a compound measured in acetone-$d_6$, i.e. 7.69 ppm (1 H, d, J=17 Hz), 7.15 ppm (2 H, br s), 6.23 ppm (1 H, d, J=17 Hz), 5.28 ppm (2 H br t), 3.33 ppm (4 H, m) and 1.78 ppm (12 H, s) as reported in *Chemical Pharmaceutical Bulletin*, Vol. 36, page 769 (1988).

(7) Chemical structure;

From these results, the crystalline compound was identified as a known compound 3-[4 -hydroxy-3,5-bis(3-methyl-2-butenyl)phenyl]-2 -propenoic acid.

The chemical structure of the crystalline compound is as shown in Chemical formula 1:

Chemical formula 1

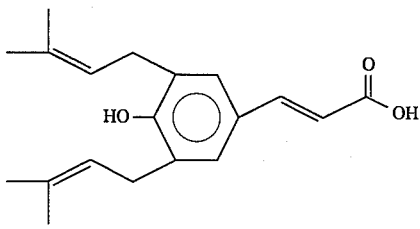

Example of Preparation 2

Preparation of Compound (2)

Two and half parts by weight, d.s.b., of the fractions, eluted with a gradient solvent system of hexane:ethyl acetate (=55:45–52:48 by volume) in the step of silica gel column chromatography in Example of Preparation 1, was fed to column chromatography using "SEPHADEX LH-20" similarly as in Example of Preparation 1. Fractions eluted at an elution position of around 1.0 (=volume of eluate/volume of carrier) were recovered. The fractions were pooled and fractionated on reverse phase high-performance liquid column chromatography. A solvent system of methanol:water:acetic acid (=900:100:0.01 by volume) was used as an eluent. The objective fractions were recovered, pooled and concentrated to obtain a crystalline compound in an amount of 0.058 parts by weight, d.s.b.

The physicochemical properties of the crystalline compound were studied:

(1) Melting point; 99° C.

(2) Elemental analysis;

Measured; C=75.14% H=6.59%

(3) Molecular weight; FD/MS, M/z=364

The molecular formula, molecular weight and elemental composition were respectively determined as $C_{23}H_{24}O_4$, 364.44 and C=75.80%, H=6.64% and O=17.56%.

(4) Ultraviolet absorption spectrum;

The crystalline compound was dissolved in methanol and measured its ultraviolet absorption spectrum.

Figure 3:
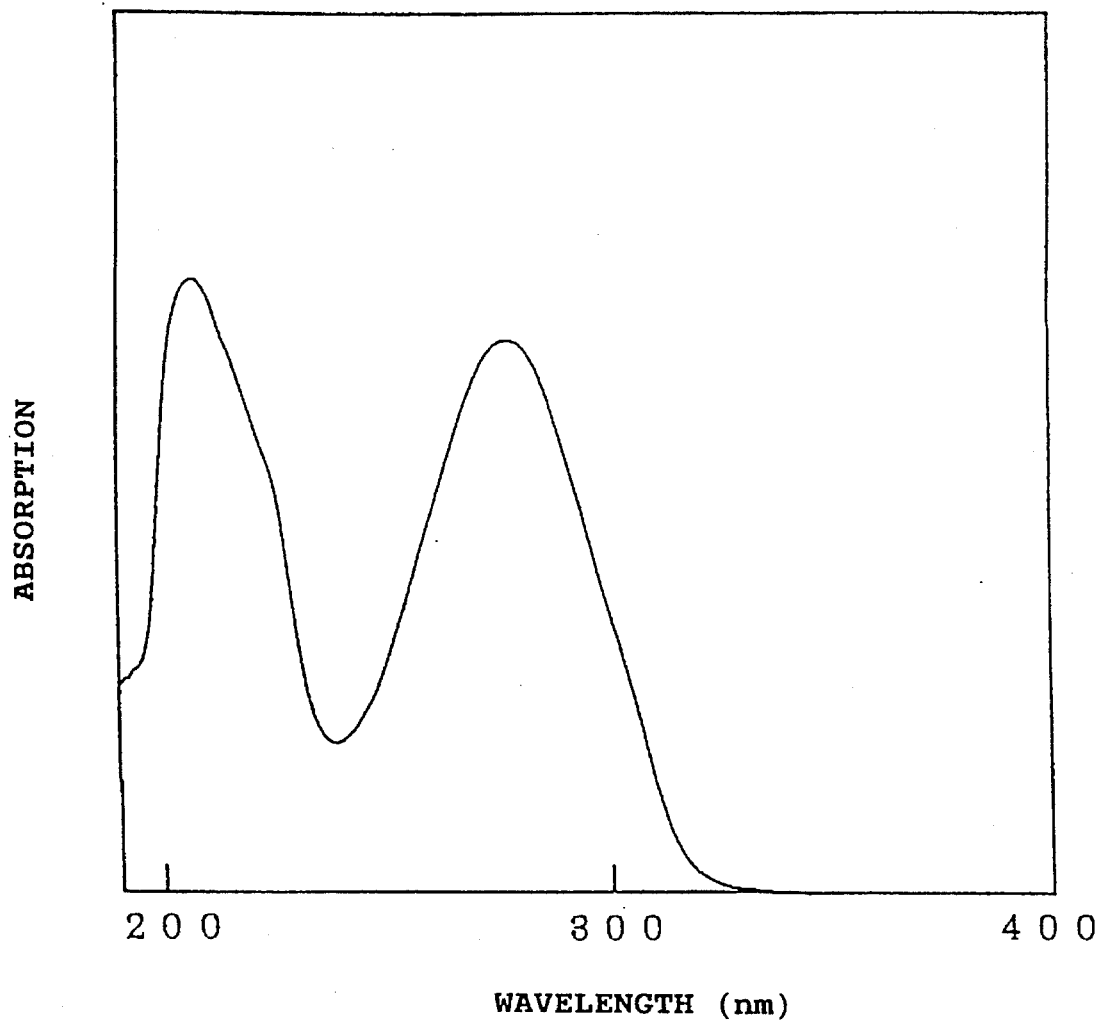
FIG. 3 shows an ultraviolet absorption spectrum of the compound (2).

The result was as shown in FIG. 3.

As evident from FIG. 3, it has the maximum absorption peaks at wavelengths of 208 nm and 278 nm.

(5) Infrared absorption spectrum;

One mg of the crystalline compound and 200 mg of dried KBr were mixed and formed into a tablet, followed by the measurement of its infrared absorption spectrum.

Figure 4:
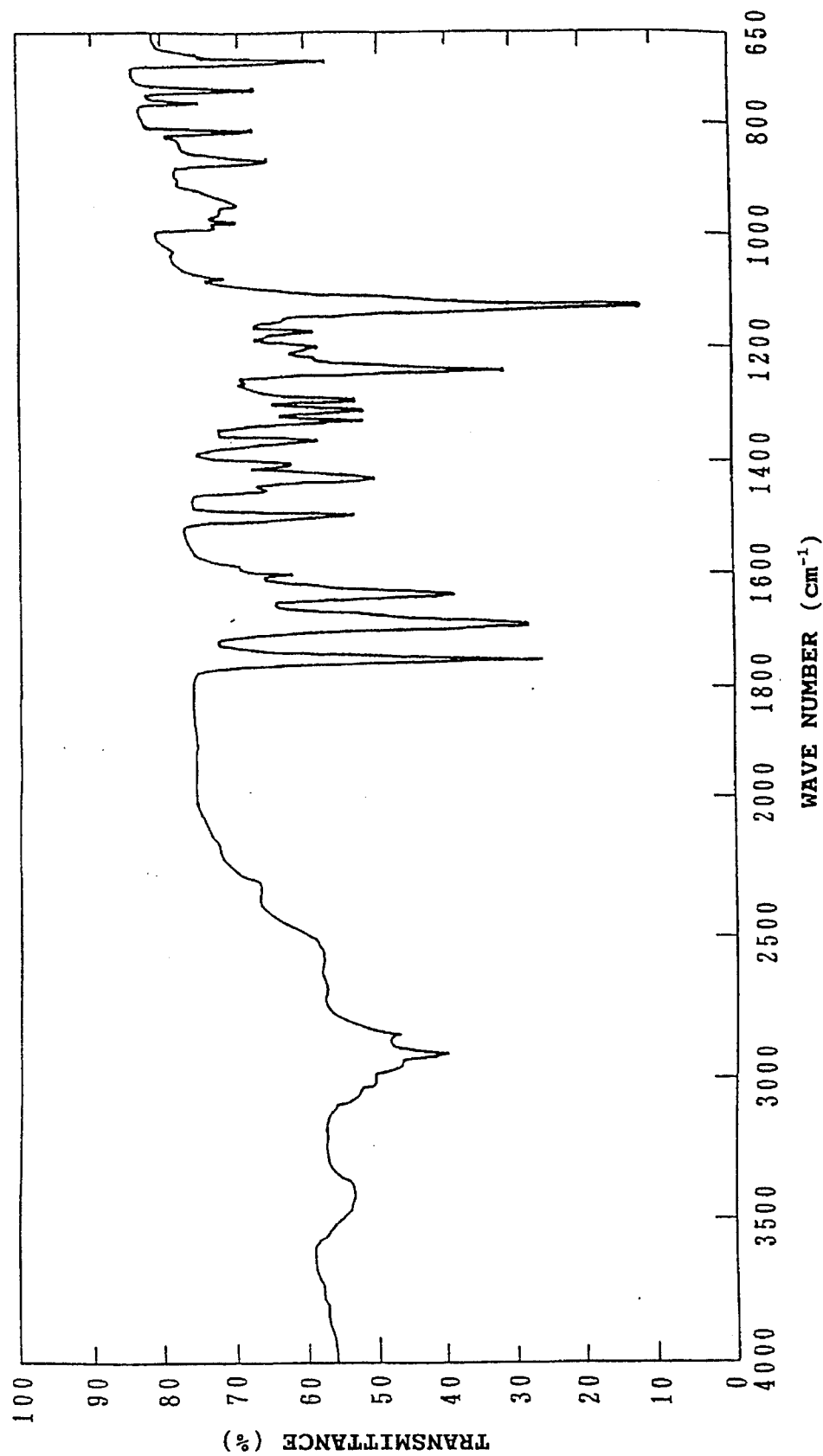
FIG. 4 shows an infrared absorption spectrum of the compound (2).

The result was as shown in FIG. 4.

As evident from FIG. 4, the crystalline compound has the absorption peaks at wave numbers of 3450 $cm^{-1}$ (br), 2920 $cm^{-1}$, 3100–2800 $cm^{-1}$ (br), 1750 $cm^{-1}$, 1690 $cm^{-1}$, 1635 $cm^{-1}$, etc (6) Analysis on nuclear magnetic resonance ($^1$H-NMR);

The crystalline compound was dissolved in deuteriumchloroform and measured its NMR with 500 MHz. The following 23 signals for hydrogen atom were detected: 7.73 ppm (1 H, d, J=16.0 Hz), 7.40 ppm (1 H, dd), 7.39 ppm (1 H, s), 7.31 ppm (2 H), 7.27 ppm (2 H), 7.24 ppm (1 H), 6.97 ppm (1 H, d, J=8.3 Hz), 6.38 ppm (1 H, d, 16.0 Hz), 5.18 ppm (1 H, br t, J=7.3, 1.4 Hz), 3.14 ppm (2 H, br d, J=7.3 Hz), 3.09 ppm (2 H, t, J=7.8, 7.4 Hz), 2.92 ppm (2 H, t, J=8.0, 7.4 Hz), 1.75 ppm (3 H, s) and 1.67 ppm (3 H, s).

These signals correspond to those of a methylester compound as reported in *Phytochemistry*, Vol. 25, page 2,841 (1986) except for a signal of methoxyl residue. The signals were 7.63 ppm (1 H, d, J=16 Hz), 7.35 ppm (1 H, dd, J=2, 8.5 Hz), 7.34 ppm (1 H, br s), 7.15– 7.3 ppm (5 H, m), 6.93 ppm (1 H, d, J=8.5 Hz), 6.33 ppm (1 H, d, 16 Hz), 5.17 ppm (1 H, tqq, J=7, 1 Hz), 3.13 ppm (2 H, br d, J=7 Hz), 3.08 ppm (2 H, br t), 2.91 ppm (2 H, br t), 1.74 ppm (3 H, br s), 1.66 ppm (3 H, br s) and 3.79 ppm (OMe, s).

(7) Chemical structure;

The crystalline compound was identified as a known compound 4-(2-carboxyethenyl)-2-(3 -methyl-2-butenyl)phenylester.

The chemical structure of the crystalline compound was as shown in Chemical formula 2:

Chemical formula 2

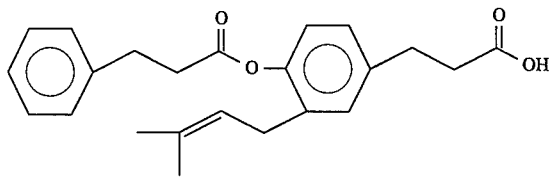

Example of Experiment 1

Effect on Growth and Regeneration of Hair

The compound (1) or (2), isolated in Example of Preparation 1 or 2, was dissolved in 50% aqueous ethanol solution containing 2% propylene glycol to give a concentration of 0.1%, 0.5% or 5.0%, and each solution was adjusted to pH 6.7 by the addition of sodium hydroxide to obtain a test solution in the form of a lotion. As a control, the same aqueous ethanol solution was used except that the compound (1) or (2) was replaced with refined water.

The dorsum surface of each rabbit was sectioned into four, about 5 $cm^2$ each, i.e. two sections near at the head side and two sections near at the tail side which were respectively bisymmetrical about the vertebral column of the rabbit, and the four sections were depilated by applying thereto a silver cream, i.e. a depilatory agent, and subjecting the rabbit to a brief standing. The depilated sections were first washed sufficiently with water, then the depilated right section near at the head side, the depilated left section near at the head side, and the depilated right section near at the tail side were respectively applied once every day by using a paintbrush with one ml of the test solution containing the compound (1), one ml of the control solution containing refined water, and one ml of the test solution containing the compound (2). The left section near at the tail side was not applied anything.

The applications of these solutions were started on the 2nd day after the depilation, and newly regenerated hairs were depilated and counted on the 10th and 20th days after the depilation. The lengths of 10 coarse hairs among regenerated hairs in each section were measured with a micromanipulator, followed by calculating the mean remainder of hair length (mm) between the length of hairs regenerated in each section of each rabbit applied with and without application.

In addition, it is known that there exists no substantial difference in the hair growth rate in the bisymmetrical dorsum surfaces about the vertebral column of a rabbit, and that there exists no substantial sexual difference in their hair growth rate.

The results were as shown in Table 1.

TABLE 1

| Test No. | Test sample | 10th day (mm) | 20th day (mm) |
|---|---|---|---|
| 1 | 0.1% of the compound (1) | 0.3 | 0.7 |
| 2 | 0.1% of the compound (2) | 0.3 | 0.6 |
| 3 | 0.5% of the compound (1) | 0.9 | 2.1 |
| 4 | 0.5% of the compound (2) | 0.8 | 1.7 |
| 5 | 5.0% of the compound (1) | 1.3 | 2.5 |
| 6 | 5.0% of the compound (2) | 1.1 | 2.1 |
| 7 | Refined water | 0.0 | 0.0 |

As evident from the results in Table 1, it was revealed that the compounds (1) and (2) exert a strong activity on the growth and regeneration of hair, and the activity is more strongly augmented when used at a concentration of 0.5% or higher.

Example of Experiment 2

Clinical Test

By using a test solution containing about one % of the compound (1) or (2), which had been revealed to exert a strong activity on the growth and regeneration of hair in Example of Experiment 1, voluntary patients with alopecia were subjected to a 3-month clinical test. As a control, refined water was used in place of the compound (1) or (2) similarly as in Example of Experiment 1. The volunteers consisted of 20 patients, 10 males and 10 females, 20-58-year-old, who were randomly chosen from those with alopecia.

The symptoms of these patients were male pattern alopecias such as alopecia prematura, alopecia presenilis and senile alopecia, and alopecia areatas such as multiple alopecia and cacoethic alopecia, and they had been received with pharmacotherapy and physiotherapy at the department of dermatology in hospitals, etc.

Since patients suffering from a slight alopecia areata may be sometimes cured without any special treatment, those, who had been diagnosed at their first diagnosis to have a relatively-small alopecic part but have no apparent alopecia, atrophia cutis and atrophic pores, were excluded in this experiment.

The volunteers were treated at the first medical treatment in a manner that their affected parts were applied with an external application to form a thin layer, well massaged, and irradiated with an artificial sunlight. They were instructed to apply the external application at their home three times a day.

The effect of the promotion of hair growth and regeneration was judged based on the following 4 ranks, i.e. "Recovered", meaning that a regeneration of hair was observed but not falling hair; "Satisfactory", meaning that the rate of hair growth and regeneration was low and the recurrence of alopecia was not observed; "Unchanged", meaning that no regeneration of hair was observed; and "Worsened", meaning that side effects and/or the promotion of falling hair were observed.

The results were as shown in Table 2.

TABLE 2

| | Therapeutic effect | | | | |
|---|---|---|---|---|---|
| Sample solution | A | B | C | D | Judgement |
| Compound (1) | 6 | 10 | 4 | 0 | Present invention |
| Compound (2) | 5 | 12 | 3 | 0 | Present invention |
| Refined water | 0 | 3 | 15 | 2 | Control |

Note: The symbol "A" means "Recovered"; "B", "Satisfactory"; "C", "Unchanged"; and "D", "Worsened".

Example of Experiment 3

Acute Toxicity

By using 7-week-old dd-strain mice, the compound (1) was orally administered to the mice for their acute toxicity. No mouse died up to a dose of 1.0 g/kg body weight. This revealed that the toxicity of the compound (1) is satisfactorily low.

The acute toxicity test of the compound (2), prepared by the method in Example of Preparation 2, was similarly conducted as above to obtain a similar result to that of the compound (1), and this indicated that the toxicity of the compound (2) was also satisfactorily low.

The followings are the preferred examples of the present invention:

Example 1

Tonic

To 55.0 parts by weight of ethanol, 2.0 parts by weight of polyoxyethylene (8) oleyl alcohol ether, and 40 parts by weight of refined water was added one part by weight of the compound (1), and the mixture was mixed with adequate amounts of μ-thujaplicin (hinikitiol), flavor and coloring agent to obtain a hair restorer in the form of a tonic.

Since the product promotes the growth and regeneration of hair, it can be used in the treatment and prevention of alopecia and falling hair, as well as dandruff and itch.

The product is suitably used as a tonic because it imparts a satisfactory flavor and refreshment.

The product has bactericidal- and anti-inflammatory-activities, and these render it arbitrarily useful as an anti-trauma agent.

Example 2

Tonic

Two parts by weight of "αG RUTIN", an α-glycosyl rutin commercialized by Toyo Sugar Refining Co., Ltd., Tokyo, Japan, and 20.0 parts by weight of glycerine were dissolved by mixing in 550 parts by weight of refined water (60 C.), and the resultant mixture was mixed with a solution prepared by dissolving in 440 parts by weight of ethanol 10 parts by weight of the compound (2) and 0.05 parts by weight of "KANKOSO 301", 6-[2-[(5-bromo-2-pyridyl)amino]vinyl]-1-ethyl-2-picolinium iodide together with a solution prepared by dissolving 2.0 parts by weight of l-menthol in 10 parts by weight of ethanol. The mixture thus obtained was filtered, and the filtrate was bottled to obtain a hair restorer in the form of a tonic.

The product which promotes the growth and regeneration of hair can be selectively used in the treatment and prevention of alopecia and falling hair, and used as a tonic to inhibit dandruff and itch.

The product has bactericidal- and anti-inflammatory-activities, and these properties render it also useful as an anti trauma agent.

Example 3

Hair Liquid

One part by weight of the compound (1) and 3.0 parts by weight of 2-O-α-D-glucopyranosyl-L-ascorbic acid were added to 55.0 parts by weight of ethanol, 20.0 parts by weight of polyoxypropylene (40) butyl ether and 13.0 parts by weight of refined water, and the resultant mixture was in usual manner mixed with adequate amounts of a pH-controlling agent, flavor, antiseptic to obtain a hair restorer in the form of a hair liquid.

The product, which promotes the growth and regeneration of hair, can be selectively used in the treatment and prevention of alopecia and falling hair, and used as a hair liquid to inhibit dandruff and inch.

The product has bactericidal- and anti-inflammatory-activities, and these properties render it also useful as an anti-trauma agent.

Example 4

Hair Cream

A hair restorer in the form of a hair cream was prepared in usual manner by mixing 3.0 parts by weight of beeswax, 15.0 parts by weight of petroleum, 42.0 parts by weight of liquid paraffin, 3.0 parts by weight of polyoxyethylene (5) ester stearate, 2.0 parts by weight of polyoxyethylene (6) oleyl alcohol ether, one part by weight of polyoxyethylene (6) cetyl alcohol ether, one part by weight of the compound (1), 0.3 parts by weight of 2-O-α-D-glucopyranosyl-L-ascorbic acid, 32.0 parts by weight of refined water, and adequate amounts of a pH-controlling agent, flavor and antiseptic.

The product, which promotes the growth and regeneration of hair, can be selectively used in the treatment and prevention of alopecia and falling hair, as well as dandruff and itch.

The product can be favorably used as a hair cream because it has a satisfiable hair gloss-imparting activity, as well as having a nutrition supplementing- and anti-inflammatory-activities to the skin.

Example 5

Ointment

A hair restorer in the form of an ointment was in usual manner prepared by mixing 10.0 parts by weight of anionic wax, self-emulsifying, 3.0 parts by weight of isopropyl myristate, 3.0 parts by weight of liquid paraffin, 4.0 parts by weight of cetanol, 5.0 parts by weight of maltose, 4.0 parts by weight of sodium salt of the compound (1), 51.0 parts by weight of refined water, and an adequate amount of an antiseptic.

The product, which promotes the growth and regeneration of hair, can be selectively used in the treatment and prevention of alopecia, falling hair, dandruff and itch.

The product has bactericidal- and anti-inflammatory-activities, and these properties render it selectively useful as a bactericide and/or an anti-inflammatory agent.

As described above, the present invention relates to a hair restorer which contains at least one compound selected from the group consisting of the compounds (1) and (2) as well as their salts. The hair restorer which exerts a strong activity on the growth and regeneration of hair can be selectively used as a cosmetic composition, pharmaceutical composition and quasi drug for the treatment and prevention of alopecia and falling hair. Thus, the present invention has a great significance in the fields of cosmetic- and pharmaceutical-industries.

We claim:

1. A topical hair restorer for alopecia which consists essentially of a carrier and an effective amount in the range of about 0.01–10 w/w % of one or more substantially pure compounds selected from the group consisting of 3-[4-hydroxy-3,5-bis(3-methyl-2-butenyl)phenyl]-2-propenoic acid, benzenepropanoic acid 4-(2-carboxyethenyl)-2-(3-methyl-2-butenyl)phenylester, and their salts as an effective ingredient.

2. The hair restorer in accordance with claim 1, wherein said carrier is a member selected from the group consisting of a cosmetically acceptable carrier, a pharmaceutically acceptable carrier, and mixtures thereof.

3. The hair restorer in accordance with claim 1, wherein said compound is in the form of a crystal.

4. A topical hair restorer for alopecia which consists of a carrier and as an effective ingredient (1) about 0.01–10 w/w % of one or more substantially pure compounds selected from the group consisting of 3-[4 -hydroxy-3,5-bis(3-methyl-2-butenyl)phenyl]-2-propenoic acid, benzenepropanoic acid 4-(2-carboxyethenyl)-2-(3-methyl-2-butenyl)phenylester, and their salts, and (2) a cyanine dye selected from the group consisting of 6-[2-[(5-bromo-2-pyridyl)amino]vinyl] -1-ethyl-2-picolinium iodide, 2-(2-anilinovinyl)-3,4-dimethyloxazolium iodide and a mixture thereof.

5. The hair restorer in accordance with claim 4, wherein the content of said cyanine dye is in the range of about 0.001–0.01 w/w %.

6. The hair restorer in accordance with claim 4, wherein said carrier is a member selected from the group consisting of a cosmetically acceptable carrier, pharmaceutically acceptable carrier, and mixtures thereof.

7. The hair restorer in accordance with claim 4, wherein said one or more compounds is in the form of a crystal.

8. A process for preparing a topical hair restorer, which comprises a step of mixing a carrier with an effective amount of about 0.01–10 w/w %, of one or more substantially pure compounds selected from the group consisting of 3-[4- hydroxy-3,5-bis(3-methyl-2-butenyl)phenyl]-2-propenoic acid, benzenepropanoic acid 4-(2-carboxyethenyl)-2-(3-methyl-2-butenyl)phenylester, and their salts as an effective ingredient.

9. The process in accordance with claim 8, wherein said carrier is a member selected from the group consisting of a cosmetically acceptable carrier, a pharmaceutically acceptable carrier, and mixtures thereof.

10. The process in accordance with claim 8, wherein said compound is in the form of a crystal.

11. The process in accordance with claim 8, wherein said compound is mixed with said carrier together with one or more cyanine dyes selected from the group consisting of 6-2-[(5-bromo-2-pyridyl)amino]vinyl]-1-ethyl-2-picolinium iodide and 2-(2-anilinovinyl)-3,4-dimethyloxazolium iodide.

12. The process in accordance with claim 11, wherein the content of said cyanine dye is in the range of about 0.001–0.01 w/w %.

* * * * *